US008502987B1

(12) United States Patent
Chipman et al.

(10) Patent No.: US 8,502,987 B1
(45) Date of Patent: Aug. 6, 2013

(54) METHOD AND APPARATUS FOR MEASURING NEAR-ANGLE SCATTERING OF MIRROR COATINGS

(75) Inventors: Russell A. Chipman, Tucson, AZ (US); Brian J. Daugherty, Tucson, AZ (US); Stephen C. McClain, Tucson, AZ (US); Steven A. Macenka, Altadena, CA (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 417 days.

(21) Appl. No.: 13/018,672

(22) Filed: Feb. 1, 2011

(51) Int. Cl.
*G01B 9/02* (2006.01)

(52) U.S. Cl.
USPC .......................................................... 356/489

(58) Field of Classification Search
USPC .......................................................... 356/489
See application file for complete search history.

(56) References Cited

U.S. PATENT DOCUMENTS

| | | | | |
|---|---|---|---|---|
| 3,432,237 A | * | 3/1969 | Flower et al. | 356/28 |
| 5,883,714 A | * | 3/1999 | Jann et al. | 356/484 |
| 5,991,034 A | * | 11/1999 | Ohtsuka | 356/511 |
| 6,154,280 A | * | 11/2000 | Borden | 356/600 |
| 6,403,966 B1 | | 6/2002 | Oka | |
| 6,477,319 B1 | | 11/2002 | Shimonaka et al. | |
| 7,218,403 B2 | | 5/2007 | Kuchel | |
| 2003/0142288 A1 | * | 7/2003 | Kinrot et al. | 356/28 |
| 2008/0030742 A1 | | 2/2008 | Hill | |

OTHER PUBLICATIONS

J. Breckinridge and B. Oppenheimer, "Polarization Effects in Reflecting Coronagraphs for White Light Applications in Astronomy",AstrophyJourn 600 (Jan. 10, 2004): 1091-98.
B. Devaraj,Takeda,Kobayashi,Usa,Chan, In vivo laser computed tomographic imaging . . . Appl. Phys. Lett. 69 (1996) pp. 3671-3673.

* cited by examiner

*Primary Examiner* — Tarifur Chowdhury
*Assistant Examiner* — Jonathon Cook
(74) *Attorney, Agent, or Firm* — Mark Homer (57) ABSTRACT

Disclosed herein is a method of determining the near angle scattering of a sample reflective surface comprising the steps of: a) splitting a beam of light having a coherence length of greater than or equal to about 2 meters into a sample beam and a reference beam; b) frequency shifting both the sample beam and the reference beam to produce a fixed beat frequency between the sample beam and the reference beam; c) directing the sample beam through a focusing lens and onto the sample reflective surface, d) reflecting the sample beam from the sample reflective surface through a detection restriction disposed on a movable stage; e) recombining the sample beam with the reference beam to form a recombined beam, followed by f) directing the recombined beam to a detector and performing heterodyne analysis on the recombined beam to measure the near-angle scattering of the sample reflective surface, wherein the position of the detection restriction relative to the sample beam is varied to occlude at least a portion of the sample beam to measure the near-angle scattering of the sample reflective surface. An apparatus according to the above method is also disclosed.

25 Claims, 5 Drawing Sheets

METHOD AND APPARATUS FOR MEASURING NEAR-ANGLE SCATTERING OF MIRROR COATINGS

STATEMENT OF GOVERNMENT INTEREST

The invention described hereunder was made in the performance of work under a NASA contract, and is subject to the provisions of Public Law #96-517 (35 U.S.C. 202) in which the Contractor has elected not to retain title.

BACKGROUND OF THE INVENTION

The present invention relates generally to the fields of optics and characterization of reflective surfaces. Specifically, it concerns an apparatus for determining the near-angle scattering of a sample reflective surface, and a method of determining the near angle scattering of a sample reflective surface using optical heterodyne detection.

The metallic coatings of reflective surfaces, e.g., mirrors, are known to have anisotropic structures that result in polarization dependent scattering behavior. These effects arc evident as small perturbations of the point spread function (PSF) known as near angle scattering. For purposes herein, near-angle scattering is defined as scattering determined at less then 10° from the centroid of the point spread function, also referred to herein as the specular reflection peak.

In addition to contributions from mirror coatings, small amounts of scattering from lenses, mounts, and/or other elements in an optical train may cause the specular peak to grow in angular extent. This combination of factors entirely overwhelms the ability to determine the near-angle scatter from a mirror sample using current methods and practices.

The Bidirectional Reflective or Scattering Distribution Function is currently measured through use of a scattering goniometer instrument, referred to in the art as a scatterometer. The instrumental beam width (collection angle span) over which a typical scatterometer responds is at least 10°, often greater then about 20° from the centroid of the point spread function. The difficulty of measuring scattering properties of coated mirrors extremely close to the specular reflection peak thus necessitates a new measurement approach.

Metallic mirror coatings have long been known to be mildly anisotropic due to the columnar nature of the metal deposition (i.e., the reflective coating.) See for example, J. Breckinridge and B. Oppenheimer, "Polarization Effects in Reflecting Coronagraphs for White Light Applications in Astronomy", *Astrophysical Journal* 600 (Jan. 10, 2004): pp. 1091-1098.

This anisotropy and its variation over a mirror surface will, to some degree, affect the scattering properties and PSF properties of the mirror. However, the terrestrial planet finder (TPF) optical system concepts currently under development require extremely small amounts of scatter at angles very near to the specular beam in order to separate the light of bright stars from that of dim orbiting planets. This is also true in a variety of technologies including telecommunications, analytical measurements, and the like, which utilize various forms of reflective surfaces to function. Measuring the polarization dependent mirror scattering properties is important to quantify the effects of surface coatings on the reflected light, and to provide metrology technology for optimizing mirror coatings for the TPF and other instruments and applications affected by near-angle scattering.

Disclosures directed to characterizing reflective surfaces include U.S. Pat. No. 6,403,966 to Oka (Oka), which is generally directed to a measurement method and a measurement apparatus for measuring the structure of a micro-structure or the structure along the depth of an object for measurement. The laser light from a solid-state laser light source is subjected to wavelength conversion to generate the ultraviolet laser light, and measurement is made of the object for measurement by heterodyne detection or homodyne detection employing the ultraviolet laser light. This enables measurement of the micro-structure of the sample. Alternatively, the laser light is split into multiple laser light beams and frequency shifted so that the laser light beams will be of different frequencies. The laser light beams are imaged at respective different focal point positions to perform heterodyne detection. The resulting heterodyne signals are separated into respective frequency bands and measurement is made of the structure of the object for measurement in association with the respective imaging points. This enables measurement of the structure of the object for measurement in the direction along its depth. Oka is directed to an apparatus and a method in which the sample being analyzed is moved within the light beam to measure surface characteristics of the sample. However, this approach does not allow for measurement and characterization of near-angle scattering of a mirror surface.

U.S. Pat. No. 5,477,319 to Shimonaka et al. (Shimonaka) is generally directed to an optical heterodyne detection method of detecting a beat signal by heterodyne detection using a superimposition of two or more beams of light including a signal beam and a reference beam. Shimonaka discloses optical heterodyne detection of scattered light, but fails to provide any disclosure or suggestion directed to an instrument or method capable of measuring near-angle scatter of a mirror.

U.S. Pat. No. 5,883,714 to Jann et al. (Jann) is generally directed to a non-contact optical inspection instrument and method for measuring the height and width of defects and contaminants on a magnetic disk surface. The instrument includes a sensor which produces an illumination beam that is modulated and then focused normally on the disk surface as a spot. The illumination spot is Doppler shifted due to the movement of the disk and the diffusely reflected light is interfered with a reference beam produced by the sensor's illumination optics. Jann discloses utilizing scattered light in an optical detection method; however, Jann fails to provide any disclosure or suggestion directed to an instrument or method capable of measuring near-angle scatter of a mirror.

U.S. Pat. No. 6,879,402 to Kuchel, and its continuation in part U.S. Pat. No. 6,972,849; and its continuation in part U.S. Pat. No. 7,218,403 (collectively referred to as Kuchel) are generally directed to interferometric scanning method(s) and apparatus for measuring optics either having aspherical surfaces or that produce aspherical wavefronts. In the disclosures, a test optic is aligned and moved with respect to a scanning axis relative to the origin of a known spherical wavefront that is generated with a reference surface to intersect the test optic at the apex of the aspherical surface and at radial zones where the spherical wavefront and the aspheric surface possess common tangents. The test surface is imaged onto a space resolving detector to form interferograms containing phase information about the differences in optical path length between the reference surface and the test surface while the axial distance which the test optic moves relative to the spherical reference surface is interferometrically measured. Kuchel discloses an apparatus and a method in which the sample being analyzed is moved within the light beam to measure surface characteristics of the sample. However, Kuchel fails to disclose or suggest a method of measuring near-angle scattering.

U.S. Patent Publication No. 20080030742 to Hill (Hill) is generally directed to an apparatus and method for in situ and ex situ measurement of spatial impulse response of an optical system using phase-shilling point-diffraction interferometry. Hill discloses a test object including: an arrangement of optical elements defining a first partially reflecting surface and a second partially reflecting surface, at least one of the first and second partially reflecting surfaces being curved, wherein the first partially reflecting surface is arranged to receive a substantially collimated input beam and produce therefrom a first transmitted beam that passes on to the second partially reflecting surface, wherein the second partially reflecting surface is arranged to receive the first transmitted beam from the first partially reflecting surface and produce a collimated second transmitted beam and a first reflected beam therefrom, wherein the first partially reflecting surface is arranged to receive the first reflected beam and produce a second reflected beam therefrom, and wherein the first and second reflecting surfaces are configured to cause the second reflecting beam to converge onto a spot on a back surface to produce a diverging beam traveling in the same direction as the collimated output beam. However, Hill fails to disclose or suggest a method of measuring near-angle scattering.

Other references of interest include J. Breckinridge and B. Oppenheimer, "Polarization Effects in Reflecting Coronagraphs for White Light Applications in Astronomy", *Astrophysical Journal* 600 (Jan 10, 2004): pp. 1091-1098; and B. Devaraj, M. Takeda, M. Kobayashi, M. Usa, and K. P. Chan, "In vivo laser computed tomographic imaging of human fingers by coherent detection imaging method using different wavelengths in near infrared region", *Appl. Phys. Lett.* 69 (1996) pp. 3671-3673.

Accordingly, a method and apparatus capable of measuring near-angle scattering is a long-felt need in the art. An apparatus and a method have been discovered which are capable of measuring near-angle scattering using coherent, heterodyne detection to enable very low noise scattering measurements of reflective coatings and other surfaces.

SUMMARY OF THE INVENTION

In one aspect of the present invention, a method of determining the near angle scattering of a sample reflective surface comprises the steps of:
a) splitting a beam of light having a coherence length of greater than or equal to about 2 meters into a sample beam and a reference beam;
b) frequency shifting both the sample beam and the reference beam to produce a fixed beat frequency between the sample beam and the reference beam;
c) directing the sample beam through a focusing lens and onto the sample reflective surface,
d) reflecting the sample beam from the sample reflective surface through a detection restriction disposed on a movable stage;
e) recombining the sample beam with the reference beam to form a recombined beam, followed by
f) directing the recombined beam to a detector and performing heterodyne analysis on the recombined beam to measure the near-angle scattering of the sample reflective surface, wherein the position of the detection restriction relative to the sample beam is varied to occlude at least a portion of the sample beam to measure the near-angle scattering of the sample reflective surface.

In another aspect of the present invention, an apparatus to measure the near angle scattering of a sample reflective surface comprises:

a) a beam of light having a coherence length of greater than or equal to about 2 meters which is directed through a beam splitter to produce a sample beam and a reference beam;
b) a frequency shifting means through which both the sample beam and the reference beam are directed to produce a fixed beat frequency between the sample beam and the reference beam;
c) one or more focusing lenses through which the sample beam is directed through which focus the sample beam on the sample reflective surface,
d) a detection restriction disposed on a movable stage through which the sample beam is reflected through from the sample reflective surface;
e) a recombining means in which the sample beam and the reference beam are recombined to form a recombined beam, followed by
f) a detector system capable of generating a signal representative of the recombined beam, wherein the detector system includes means for performing heterodyne analysis on the detector signal produced by the recombined beam to measure the near-angle scattering of the sample reflective surface, wherein the position of the detection restriction relative to the sample beam is dimensioned and arranged to be varied to occlude at least a portion of the sample beam reflected from the sample reflective surface to measure the near-angle scattering of the sample reflective surface.

The foregoing has outlined the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

In the following description, numerous specific details are set forth to provide a thorough understanding of the present invention. However, it will be obvious to those skilled in the art that the present invention may be practiced without such specific details. In other instances, well-known devices have been shown in block diagram form in order not to obscure the present invention in unnecessary detail. For the most part, details unnecessary to obtain a complete understanding of the present invention have been omitted in as much as such details are within the skills of persons of ordinary skill in the relevant art.

In keeping with long-standing patent law convention, the words "a" and "an" when used in the present specification in concert with the word comprising, including the claims, denote "one or more." Description in which the term "comprising" is used may also include more limiting embodiments such as "consisting essentially of" and "consisting of". The term comprising is used herein for brevity.

Broadly, the present invention generally provides a method and an apparatus to measure the near angle scattering of a sample reflective surface. The instrument utilizes optical heterodyne detection to measure the near-angle scattering of mirrors and/or other reflective surfaces. An embodiment of the Optical Heterodyne Near-angle Scatterometer (OHMS) according to the instant disclosure comprises:

a) a beam of light having a coherence length of greater than or equal to about 2 meters which is directed through a beam splitter to produce a sample beam and a reference beam;

b) a frequency shifting means through which both the sample beam and the reference beam are directed to produce a fixed beat frequency between the sample beam and the reference beam;

c) one or more focusing lenses through which the sample beam is directed through which focus the sample beam on the sample reflective surface, d) a detection restriction disposed on a movable stage through which the sample beam is reflected through from the sample reflective surface;

e) a recombining means in which the sample beam and the reference beam are recombined to form a recombined beam, followed by f) a detector system capable of generating a signal representative of the recombined beam, wherein the detector system includes means for of performing heterodyne analysis on the detector signal produced by the recombined beam to measure the near-angle scattering of the sample reflective surface, wherein the position of the detection restriction relative to the sample beam is dimensioned and arranged to be varied to occlude at least a portion of the sample beam reflected from the sample reflective surface to measure the near-angle scattering of the sample reflective surface.

Figure 1:
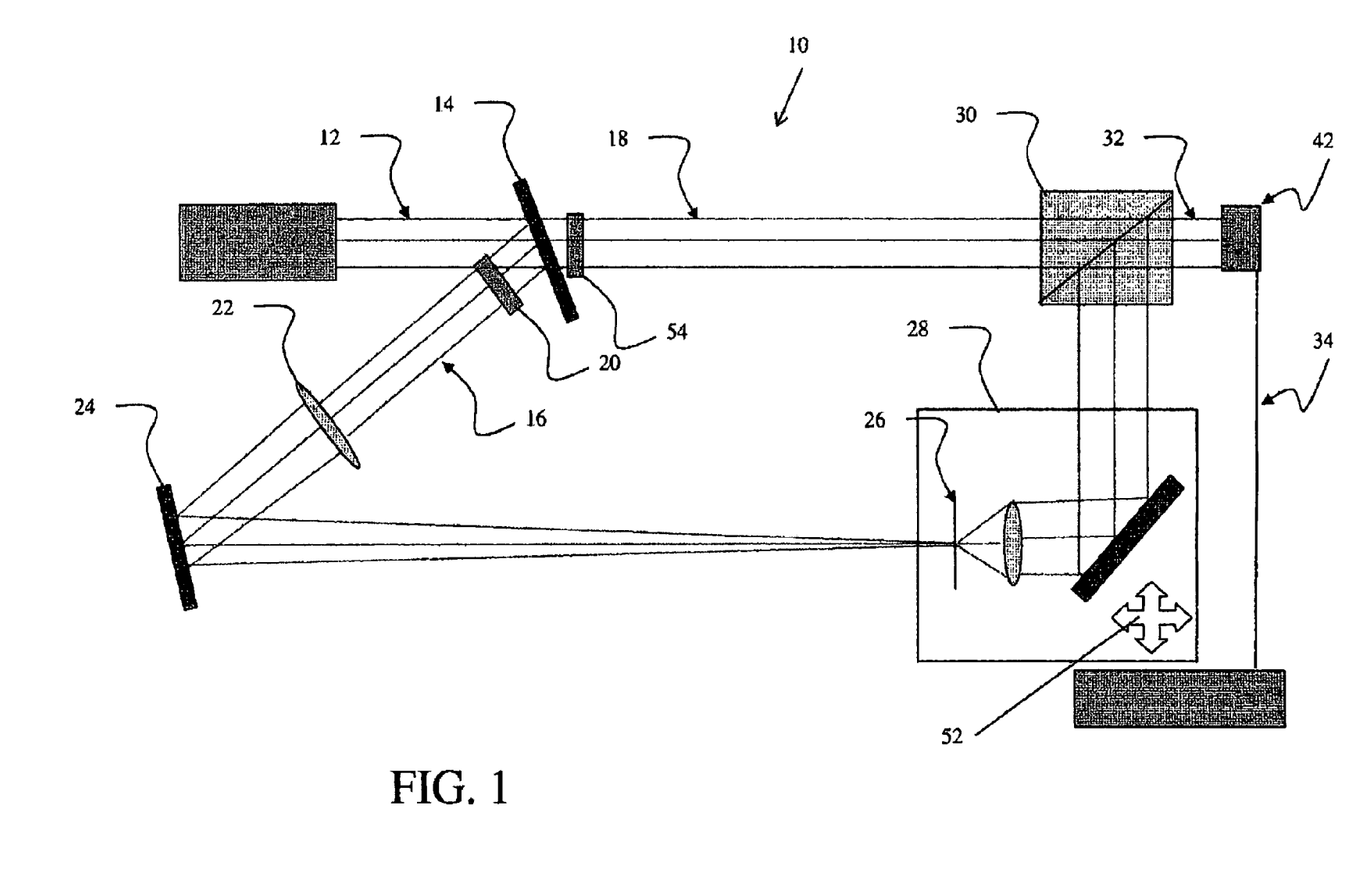
FIG. 1 is block diagram showing an arrangement and interplay of the various components of an embodiment of the Optical Heterodyne Near-angle Scatterometer (OHNS) according to the instant disclosure.

Turning now to the Figures, FIG. 1 shows an embodiment of the Optical Heterodyne Near-angle Scatterometer, also referred to as the OHNS (10) in block diagram format. The OHNS (10) includes a beam of light having a coherence length of greater than or equal to about 1 meter (12) which is directed through a beam splitter (14) to produce a sample beam (16) and a reference beam (18.) The sample beam 16 is then directed through a sample frequency shifting means (20) and the reference beam 18 is simultaneously directed through a reference frequency shifting means (54) to produce a fixed beat frequency between sample beam 16 and reference beam 18. The fixed beat frequency between sample beam 16 and reference beam 18 is consistent with heterodyne detection principles and practice as known to one of skill in the art. Sample beam 16 is then directed through one or more focusing lenses (22) which focus sample beam 16 on the detection restriction (26) while illuminating the sample reflective surface 24. Sample beam 16 is then reflected from sample reflective surface 24 through a detection restriction 26 disposed on a movable stage (28). Movable stage 28 is capable of x-y translation. Sample beam 16 is then recombined with reference beam 18 using a recombination means (30) to produce a recombined beam (32). Recombined beam 32 is then directed onto a photo-detector 42 in electronic communication with detector system (34) to produce a signal representative of recombined beam 32.

Detector system 34 includes means for performing heterodyne analysis on the detector signal produced by recombined beam 32 to measure the near-angle scattering of sample reflective surface 24. To obtain the near angle scattering of sample reflective surface 24, the position of detection restriction 26 relative to sample beam 16 is dimensioned and arranged to be varied to occlude at least a portion of sample beam 16 passing through detection restriction 26 which is subsequently recombined with reference beam 18 to produce recombined beam 32 to measure the near-angle scattering of sample reflective surface 24.

It is to be understood that each time sample beam 16 and/or reference beam 18 passes through a component of the optical heterodyne near-angle scatterometer, the characteristics of the light beam are changed in some fashion. However, for purposes herein, sample beam 16 and reference beam 18 have been labeled consistently as such regardless of the effect a particular component or the sample reflective surface 24 may have on the properties of sample beam 16 or reference beam 18 in order to clarify the path taken by sample beam 16 and reference beam 18 while characterizing and/or determining the near angle scattering of sample reflective surface 24.

Figure 2:
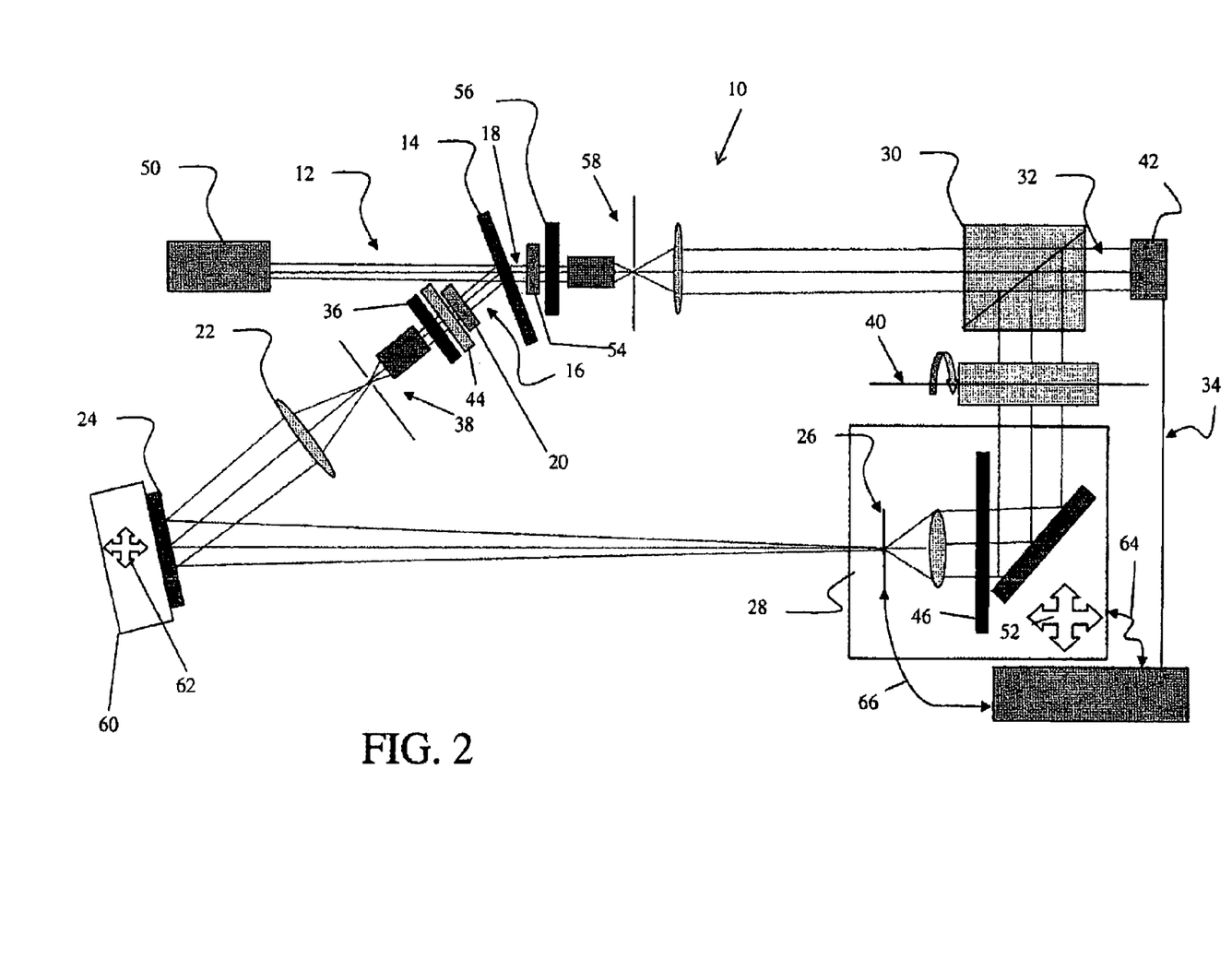
FIG. 2 is block diagram showing an arrangement and interplay of the various components of an alternative embodiment of the Optical Heterodyne Near-angle Scatterometer (OHNS) according to the instant disclosure.

FIG. 2 shows another embodiment of the OHNS wherein, in addition to the path and components described in FIG. 1, sample beam 16 is further directed through a half waveplate (44), followed by a sample polarizer (36), and then through a Sample spatial filter system (38) prior to being directed through focusing lens 22. The portion of Sample beam 16 reflected from sample reflective surface 24 and through detection restriction 26 is also directed through an analyzer polarizer 46 which functions as a polarization state analyzer for sample beam 16. Likewise, reference beam 18 is directed through a reference polarizer (56) and then through a reference spatial filter system (58) prior to being recombined with sample beam 16. In an embodiment, Sample beam 16 is also directed through a movable plane parallel plate (40) that may be oriented to shift sample beam 16 prior to being recombined with reference beam 18. In an embodiment, recombined beam 32 strikes photo detector 42, preferably a Si photodiode detector, which is in electronic communication with detector system 34.

The near-angle scattering of sample reflective surface is determined by varying the position of detection restriction 26 relative to sample beam 16 such that at least a portion of sample beam 16 reflected from sample reflective surface 24 is occluded prior to being recombined with reference beam 18. Detector system 34 then generates a signal representative of recombined beam 32. Heterodyne analysis is then performed on the detector signal produced by recombined beam 32 to measure the near-angle scattering of sample reflective surface 24.

In an embodiment, sample reflective surface 24 is mounted on a variable position sample mount (60) which may be held in a constant position while raster scanning 52 the position of detection restriction 26 relative to sample beam 16 is performed. In an embodiment, variable position sample mount 60 may be varied (62) such that the position of sample reflective surface 24 is varied separately or in tandem with raster scanning 52 of detection restriction 26 relative to sample beam 16 to characterize sample reflective surface 24.

In an embodiment, beam of light 12 is produced using a laser (50). In a preferred embodiment, beam of light 12 has a coherence length of greater than or equal to about 2 meters, preferably greater than or equal to about 10 meters, preferably greater than or equal to about 50 meters, preferably greater than or equal to about 100 meters, more preferably greater than or equal to about 150 meters. In an embodiment, beam of light 12 is produced using a 532 nm laser, an ultra-violet (UV) laser, or the like.

In an embodiment, sample frequency shifting means 20 and/or reference frequency shifting means 54 each comprise an acousto-optic modulator (AOM), also referred to in the art as a Bragg cell, which uses the acousto-optic effect to diffract and shift the frequency of light using sound waves. The properties of the sample beam 16 and the reference beam 18 exiting the AOM may be controlled using deflection, intensity, frequency, phase, and/or polarization aspects of the AOM. In an embodiment, sample frequency shifting means 20 and/or reference frequency shifting means 54 each comprise an electro-optic modulator to frequency shift the particular beam.

In an embodiment, beam splitter 14 splits beam of light 12 into two equal portions such that the ratio of the intensity of sample beam 16 to reference beam 18 is about 1:1. In a preferred embodiment, the ratio of the intensity of sample beam 16 to reference beam 18 is greater than or equal to about 60:40, preferably greater than or equal to about 70:30, preferably greater than or equal to about 80:20, with greater than or equal to about 90:10 being still more preferred. In an embodiment, there is preferably enough light in the reference beam to achieve shot noise limited detection, as is readily understood by one of minimal skill in the art. In an embodiment, a laser having at least 15 mW power output is used, preferable at least 50 mW, with greater than or equal to 200 mW being still more preferred.

In an embodiment, unwanted scattered light may be reduced using low scattering focusing lenses in the active path and/or by using sample spatial filter system 38 and reference spatial filter system 58 to block scattered light from all of the elements prior to the focusing lens 22. This approach allows for removal of essentially all scattered light except for that produced by focusing lens 22. In an embodiment, focusing lens 22 is an uncoated, highly polished focusing lens which produces a minimal amount of scattered light relative to the measurement of the near angle scattering of sample reflective surface 24.

It has been discovered that a relatively large "spot" of light may be directed to and reflected from sample reflective surface 24 to better characterize the near-angle scattering thereof. Accordingly, focusing lens 22 may have an f-ratio of greater than or equal to about 30, preferably greater than or equal to about 50, preferably greater than or equal to about 100, preferably greater than or equal to about 200, preferably greater than or equal to about 300, preferably greater than or equal to about 400, with greater than or equal to about 500 being still more preferred.

In an embodiment, detection restriction 26 is a pinhole mounted on movable stage 28, which is capable of x-y translation. In an embodiment, movable stage 28 is in electronic communication (shown in FIG. 2 as Numbered Item 64) with detector system 34 such that raster scanning of sample beam 16 is computer controlled. In an embodiment, detection restriction 26 has a fixed size through which at least a portion of sample beam 16 reflected from sample reflective surface 24 may pass. In an alternative embodiment, detection restriction 26 is variable in size and may be controlled by the detector system (shown in FIG. 2 as Numbered Item 66). By raster scanning 52 detection restriction 26 (also referred to herein as a "detection pinhole") across the image plane formed by the reflected sample beam 16, the OHNS is able to obtain an extremely high resolution image of the PSF. The OHNS is also able to obtain the highest possible contrast when scanning through the nulls of the PSF.

In an embodiment, recombination means 30 comprises a non-polarizing beam splitter. Detector 42 of detector system 34 may include a Si photodiode or the like, which is capable of generating an electronic or other signal representative of recombined beam 32. Detector system 34 may also include a computer in electronic communication with the various components of the OHNS capable of being varied. In an embodiment, detector system 34 includes a spectrum analyzer which utilizes heterodyne detection to determine the near angle scattering of sample reflective surface 24. In an embodiment, coherent detection is used to allow for measurements to be made with a very large dynamic range and high sensitivity. While non-coherent detection is possible with the OHNS, coherent detection is preferably due to the expectation that scattered light levels from telescope mirrors may be many orders of magnitude lower than specular light. However, the type of detection utilized is dependent on the type of sample reflective surface, and the wavelengths of the electromagnetic radiation being utilized.

In an embodiment, the OHNS described herein is capable of measuring near-angle scattered light levels which are less than or equal to about $10^{12}$ times below the intensity of the specular light. In an embodiment, the detection system has a dynamic range of greater than or equal to about 140 dB, and a noise equivalent power (NEP) of less than or equal to about $10^{-17}$ W. In an embodiment, the OHNS is capable of measuring the near angle scattering such that a first specular light ring is resolved from the point spread function at less than 1° from the centroid of the point spread function, preferably less then or equal to about 100 arcseconds, more preferably less than or equal to about 50 arcseconds, more preferably less than or equal to about 40 arcseconds, more preferably less than or equal to about 30 arcseconds, more preferably less than or equal to about 20 arcseconds, more preferably less than or equal to about 10 arcseconds from the centroid of the point spread function.

As shown in FIG. 2, an embodiment of the OHNS may comprise polarization capability to characterize the polarization effects various coatings may have on sample reflective surface 24. Polarization control may be implemented by placing sample polarizer 36, which is a generator polarizer, before sample reflective surface 24 and analyzer polarizer 46 after detection pinhole 26. In an embodiment, half-wave plate 44 is placed before sample polarizer 36 to rotate the polarization state of sample beam 16 emerging from laser 50 to maximize transmission through sample polarizer 36 when it is set at different angles. In an embodiment, sample polarizer 36 is set to illuminate sample reflective surface 24 with either "s-" or "p-" polarized light so the effects of different types of illumination on sample reflective surface 24 can be measured. In an embodiment, the illumination state may be limited to s- and p-polarized light since the sample reflective surface is illuminated at a non-zero angle and thus, there would be polarization aberrations if other illumination states were used. In an embodiment, analyzer polarizer 46 may be rotated to be either parallel too, or perpendicular with the orientation of sample polarizer 36 to measure the cross coupled polarization cause by light interaction with the sample reflective surface, e.g., a metallic mirror coating. In an embodiment, a reference polarizer 56 may be set to produce reference beam 18 oriented at an angle of about 45° to produce a reference beam 18 having an equal amount of vertical and horizontal polarized light to interfere with the sample beam 16. In another embodiment, reference polarizer 56 may be set to produce reference beam 18 oriented at an angle of greater than or equal 0° and less than or equal to about 45° relative to sample beam 16. In yet another embodiment, sample polarizer 36 and reference polarizer 56 may be rotated such that when reference beam 18 and sample beam 16 are recombined, both beams will have the same polarization.

EXAMPLES

Figure 3A:
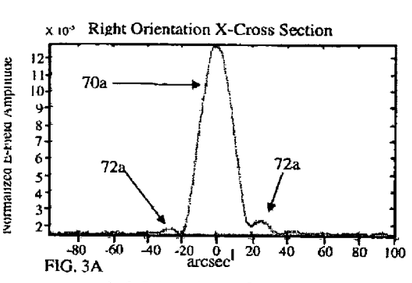
FIGS. 3A-3D show a set of cross polarized data taken of a sample mirror having an anisotropic coating with the method according to the instant disclosure.
Figure 3B:
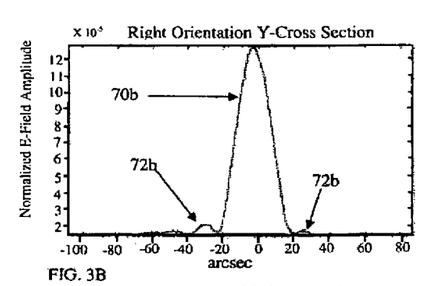
Figure 3C:
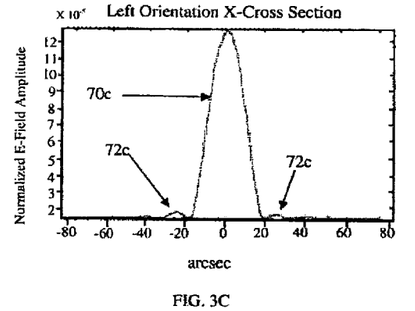
Figure 3D:
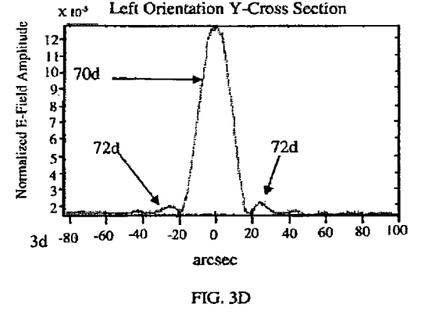
Figure 4A:
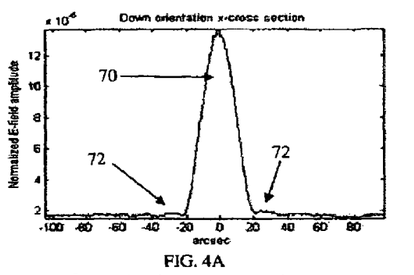
FIGS. 4A-4D show representations of a set of cross polarized data taken of a sample mirror having an anisotropic coating with the method according to the instant disclosure.
Figure 4B:
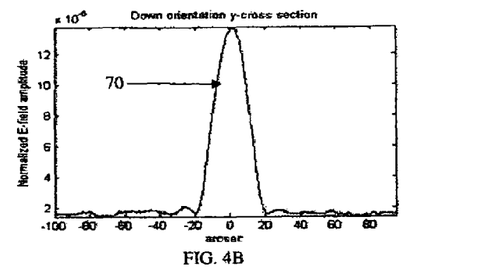
Figure 4C:
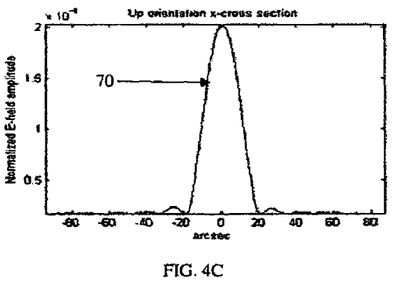
Figure 4D:
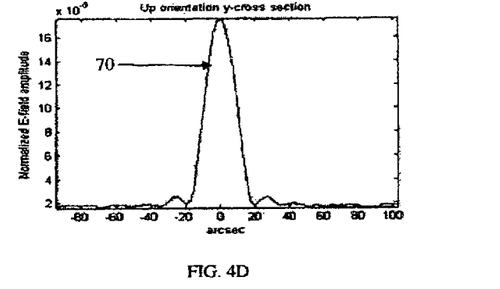

A sample designed to display oblique columnar microstructure was fabricated and measured. The sample was fabricated by applying a silver coating to one side of an interference flat with a 45° deposition angle. During the analysis and measurement, the samples were oriented relative to the orientation of the deposition angle. The first set of cross polarized data taken of the anisotropic sample is shown in FIGS. 3A-3D, wherein:

FIG. 3A, shows a scan through the image in the horizontal direction with the sample oriented so the columnar microstructure is angled down from the optical axis;

FIG. 3B shows a scan through the image in the vertical direction with the sample oriented so the columnar microstructure is angled down from the optical axis;

FIG. 3C shows a scan through the image in the horizontal direction with the sample oriented with the columnar structure pointed up; and FIG. 3D shows a scan through the image in the vertical direction with the sample oriented so the columnar microstructure is pointed up from the optical axis.

Accordingly, FIG. 3A, shows the point spread function 70 of the sample oriented in the downward orientation, x-cross section;

FIG. 3B shows the point spread function 70 of the sample oriented in the downward orientation, y-cross section;

FIG. 3C shows the point spread function 70 of the sample oriented in the upward orientation, x-cross section; and FIG. 3D shows the point spread function 70 of the sample oriented in the upward orientation y-cross section. FIGS. 3A-3D show anisotropic depolarization effects. The effects appear in the specular light in the first ring 72 of the PSF 70 (shown in FIG. 3A). This effect is most pronounced in FIGS. 3C) and 3D). Both plots are asymmetric but the asymmetry is in the opposite direction depending on the orientation of the sample. The results suggest that light reflected from the sample has a different polarization signature depending on the orientation of the columnar microstructure of the mirror coating. The sample was illuminated with horizontally polarized light during these measurements. As the data shows, the near angle scattering has been measured at 20 arcsec or less using the method and apparatus as described herein.

The data shown in FIGS. 4A-4D is similar to that in FIGS. 3A-3D, but the sample is oriented with the columnar microstructure facing up or down instead of right or left. The asymmetry seen in FIGS. 3A-3D is not present in FIGS. 4A-4D. The plots in FIGS. 4A-4D are approximately symmetric and do not display a significant sample orientation based difference. These results suggest that there is more effect when the coating anisotropy is aligned in the direction of the electric field of a polarized beam than when it is normal to the direction of polarization.

Figure 5:
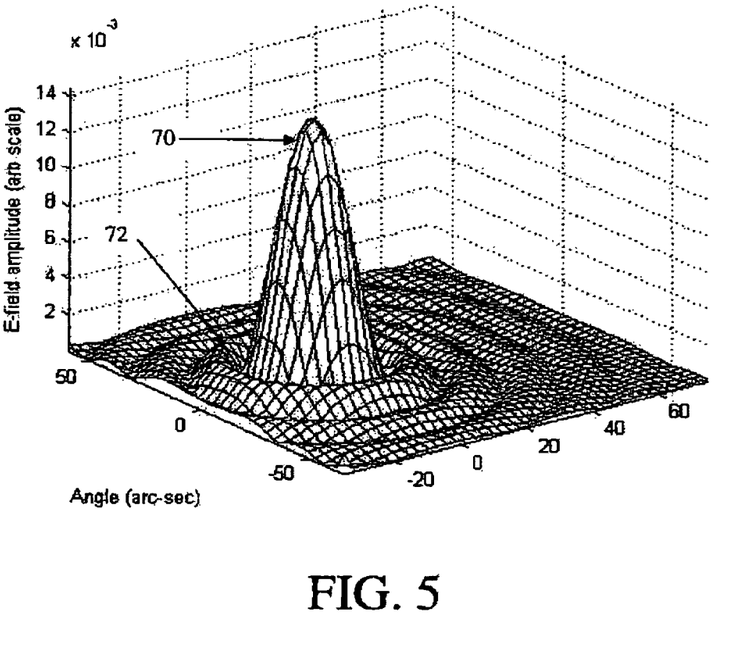
FIG. 5 is a full scan representation of data taken of a sample mirror having an anisotropic coating with the method according to the instant disclosure.

FIG. 5 shows the result of raster-scanning the detection pinhole through the focal plane of the sample beam using a parallel sample polarization generator and analyzer polarizer. The PSF,(70) is shown as are the first specular light ring 72, and subsequent specular light rings. The plot represents a full scan of the anisotropic mirror sample taken with the columnar microstructure oriented to the right. The plot in FIG. 5 shows electric field amplitude instead of irradiance.

The data shown in FIG. 5 may be further de-convoluted to allow for a 2D scattered light plot from 2D measurements. As shown in FIG. 5, the scattered light is measured directly in the nulls of the PSF.

The new measurement system described herein, using coherent optical detection methods for the measurement of near angle scattered light shows the utility of this measurement method for mirror samples. As the results show, the method and apparatus described herein is able to accurately measure the PSF of light reflected from a metallic mirror coating. The results also showed evidence of anisotropic polarization effects caused by reflection from anisotropic columnar microstructure found in metallic mirror coatings; a result previously speculated to exist, yet until now beyond the ability of known systems to measure.

Accordingly, the data shows that the OHNS is capable of measuring near-angle light scattering of the sample mirror at less than 100 arcseconds; light that would otherwise have been obscured using conventional means known in the art.

All patents and publications mentioned in the specification are indicative of the level of those skilled in the art to which the invention pertains. All patents and publications are herein incorporated by reference to the same extent as if each individual publication was specifically and individually indicated to be incorporated by reference.

It should be understood, of course, that the foregoing relates to preferred embodiments of the invention and that modifications may be made without departing from the spirit and scope of the invention as set forth in the following claims.

We claim:

1. A method of determining the near angle scattering of a sample reflective surface comprising the steps of:
    a) splitting a beam of light having a coherence length of greater than or equal to about 2 meters into a sample beam and a reference beam;
    b) frequency shifting both the sample beam and the reference beam to produce a fixed beat frequency between the sample beam and the reference beam;
    c) directing the sample beam through a focusing lens and onto the sample reflective surface,
    d) reflecting the sample beam from the sample reflective surface through a detection restriction disposed on a movable stage;
    e) recombining the sample beam with the reference beam to form a recombined beam, followed by
    f) directing the recombined beam to a detector and performing heterodyne analysis on the recombined beam to measure the near-angle scattering of the sample reflective surface, wherein the position of the detection restriction relative to the sample beam is varied to occlude at least a portion of the sample beam to measure the near-angle scattering of the sample reflective surface.

2. The method of claim 1, wherein the beam of light is produced using a laser.

3. The method of claim 1, wherein the beam of light is produced using an ultra-violet laser.

4. The method of claim 1, wherein the frequency shifting is produced using acousto-optic modulators.

5. The method of claim 1, wherein the focusing lens has an f-ratio of greater than or equal to about 30.

6. The method of claim 1, wherein the detection restriction is a pinhole.

7. The method of claim 1, wherein the sample beam passes through a polarizer prior to passing through the focusing lens, and wherein the reference beam passes through a polarizer prior to being recombined with the sample beam.

8. The method of claim 7, wherein the sample beam is directed through a polarization state analyzer prior to being recombined with the reference beam.

9. The method of claim 1, wherein the sample beam passes through a spatial filter prior to passing through the focusing lens, and wherein the reference beam passes through a spatial filter prior to being recombined with the sample beam.

10. The method of claim 1, wherein the position of the detection restriction relative to the sample beam is varied to occlude at least a portion of the sample beam to measure the near-angle scattering of the sample reflective surface includes the step of raster-scanning the detection restriction through a focal plane of the sample beam.

11. The method of claim 10, wherein the near angle scattering is measured in the nulls of the point spread function obtained by varying the detection restriction relative to the sample beam.

12. The method of claim 1, wherein the sample reflective surface is varied relative to a structure of the coating of the sample reflective surface.

13. The method of claim 1, wherein a first specular light ring is resolved from the point spread function at less than 1° from the centroid of the point spread function.

14. The method of claim 1, wherein a first specular light ring is resolved from the point spread function at less than 50 arcseconds from the centroid of the point spread function.

15. An apparatus to measure the near angle scattering of a sample reflective surface comprising:
   a) a beam of light having a coherence length of greater than or equal to about 2 meters which is directed through a beam splitter to produce a sample beam and a reference beam;
   b) a frequency shifting means through which both the sample beam and the reference beam are directed to produce a fixed beat frequency between the sample beam and the reference beam;
   c) one or more focusing lenses through which the sample beam is directed through which focus the sample beam on the sample reflective surface,
   d) a detection restriction disposed on a movable stage through which the sample beam is reflected through from the sample reflective surface;
   e) a recombining means in which the sample beam and the reference beam are recombined to form a recombined beam, followed by
   f) a detector system capable of generating a signal representative of the recombined beam, wherein the detector system includes means for of performing heterodyne analysis on the detector signal produced by the recombined beam to measure the near-angle scattering of the sample reflective surface, wherein the position of the detection restriction relative to the sample beam is dimensioned and arranged to be varied to occlude at least a portion of the sample beam to measure the near-angle scattering of the sample reflective surface.

16. The apparatus of claim 15, wherein the beam of light is produced using a laser.

17. The apparatus of claim 15, wherein the beam of light is produced using an ultra-violet laser.

18. The apparatus of claim 15, wherein the frequency shifting means comprises an acousto-optic modulator.

19. The apparatus of claim 15, wherein the one or more focusing lenses have an effective f-ratio of greater than or equal to about 30.

20. The apparatus of claim 15, wherein the detection restriction is a pinhole.

21. The apparatus of claim 15, further comprising a first polarizer means arranged such that the sample beam passes through the first polarizer means prior to passing through the focusing lens, and a second polarizer means arranged such that the reference beam passes through the second polarizer means prior to being recombined with the sample beam.

22. The apparatus of claim 21, further comprising a polarization state analyzer arranged such that the sample beam passes through the polarizer state analyzer after being reflected from the sample reflective surface, but prior to being recombined with the reference beam.

23. The apparatus of claim 15, further comprising a first spatial filter means arranged such that the sample beam passes through the first spatial filter means prior to passing through the focusing lens, and a second spatial filter means arranged such that the reference beam passes through the second spatial filter means prior to being recombined with the sample beam.

24. The apparatus of claim 15, wherein the detection restriction is mounted to a movable stage such that the position of the detection restriction relative to the sample beam may be varied to occlude at least a portion of the sample beam to measure the near-angle scattering of the sample reflective surface by raster-scanning the detection restriction through a focal plane of the sample beam.

25. The apparatus of claim 15, wherein the sample reflective surface may be varied relative to a structure of the coating of the sample reflective surface.

* * * * *